(12) United States Patent
Ritschl

(10) Patent No.: US 11,704,845 B2
(45) Date of Patent: Jul. 18, 2023

(54) TOMOSYNTHESIS METHOD

(71) Applicant: Siemens Healthcare GmbH, Erlangen (DE)

(72) Inventor: Ludwig Ritschl, Buttenheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 371 days.

(21) Appl. No.: 17/023,893

(22) Filed: Sep. 17, 2020

(65) Prior Publication Data
US 2021/0097735 A1    Apr. 1, 2021

(30) Foreign Application Priority Data
Sep. 27, 2019   (DE) .................. 10 2019 214 932.4

(51) Int. Cl.
*A61B 6/00*   (2006.01)
*G06T 11/00*  (2006.01)
*A61B 6/02*   (2006.01)

(52) U.S. Cl.
CPC ............ *G06T 11/003* (2013.01); *A61B 6/025* (2013.01); *A61B 6/4078* (2013.01);
(Continued)

(58) Field of Classification Search
CPC ....... A61B 6/025; A61B 6/4078; A61B 6/463; A61B 6/027; A61B 6/4021; A61B 6/466;
(Continued)

(56) References Cited

U.S. PATENT DOCUMENTS

| 10,314,564 B2 | 6/2019 | Weingarten et al. |
| 2012/0257714 A1* | 10/2012 | Graumann ........... A61B 6/5205 378/19 |
| 2019/0117180 A1 | 4/2019 | Gemmel et al. |

FOREIGN PATENT DOCUMENTS

| DE | 4235183 A1 | 3/1995 |
| DE | 4235183 A1 | 3/1995 |
(Continued)

OTHER PUBLICATIONS

Luckner Christoph et al. "Parallel-Shift Tomosynthesis for Orthopedic Applications" Proc. SPIE 10573, Medical Imaging 2018: Physics of Medical Imaging, 105730G (Mar. 9, 2018); https://doi.org/10.1117/12.2292384.

*Primary Examiner* — Dani Fox
(74) *Attorney, Agent, or Firm* — Harness, Dickey & Pierce, P.L.C.

(57) ABSTRACT

A method includes recording a plurality of projection recordings along a linear trajectory. An X-ray source and an X-ray detector move in parallel opposite to one another along the linear trajectory and the examination object is arranged between the X-ray source and the X-ray detector. The method includes reconstructing a tomosynthesis dataset, respective depth information of the examination object is respective determined along an X-ray beam bundle spanned by the motion along the linear trajectory and an X-ray beam fan of the X-ray source perpendicular to the linear trajectory so that different respective depth levels in the object parallel to a detection surface of the X-ray detector are respectively scanned differently. Finally, the method includes determining a first slice image with a first slice thickness in a depth level, among the respective depth levels, substantially parallel to the detection surface of the X-ray detector based on the tomosynthesis dataset.

17 Claims, 3 Drawing Sheets

(52) U.S. Cl.
CPC ............ *A61B 6/4452* (2013.01); *A61B 6/463* (2013.01); *A61B 6/5241* (2013.01); *G06T 2210/41* (2013.01)

(58) Field of Classification Search
CPC ......... A61B 6/469; A61B 6/5235; A61B 6/54; A61B 6/4085; A61B 6/4452; A61B 6/5205; A61B 6/5241; G06T 2207/10112; G06T 2207/10116; G06T 2207/30008; G06T 7/33; G06T 7/38; G06T 7/593; G06T 11/003; G06T 11/006; G06T 2210/41; G06T 2210/436
See application file for complete search history.

(56) References Cited

FOREIGN PATENT DOCUMENTS

| | | |
|---|---|---|
| EP | 3473185 A1 | 4/2019 |
| EP | 3473185 A1 | 4/2019 |

\* cited by examiner

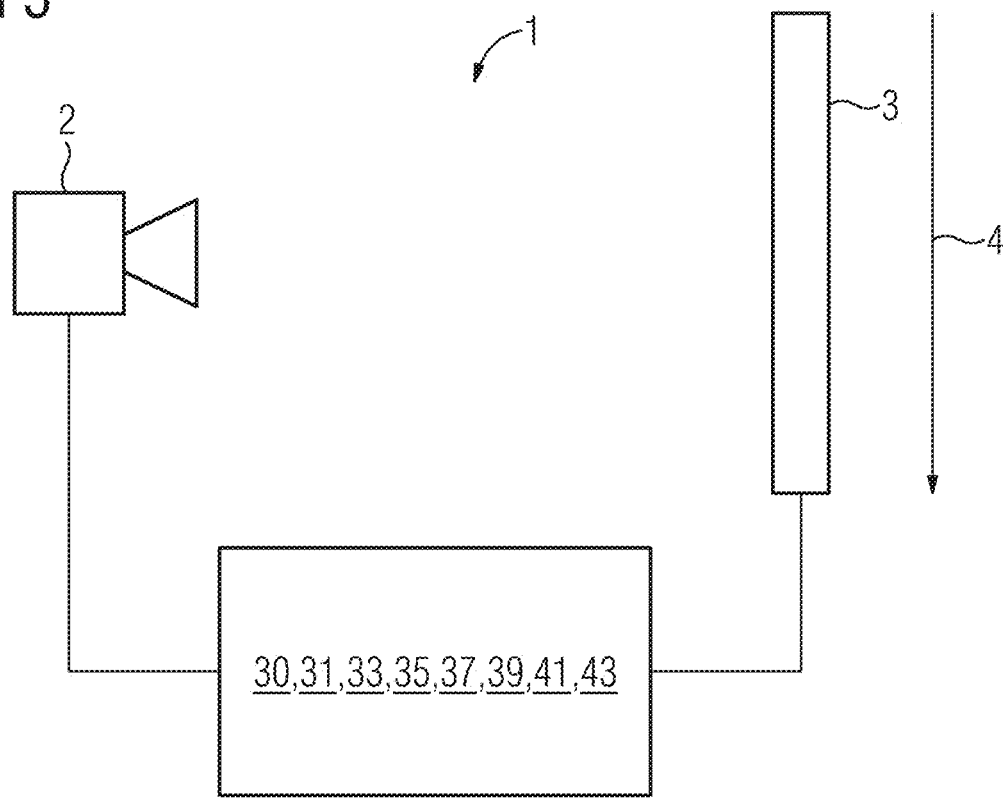

TOMOSYNTHESIS METHOD

PRIORITY STATEMENT

The present application hereby claims priority under 35 U.S.C. § 119 to German patent application number DE 102019214932.4 filed Sep. 27, 2019, the entire contents of which are hereby incorporated herein by reference.

FIELD

Embodiments of the invention generally relate to a method for determining a first slice image of a tomosynthesis recording of an examination object and in particular the further determination of a second thicker slice image, wherein different depth levels in the object parallel to the detection surface are scanned differently.

BACKGROUND

Tomosynthesis methods are usually used for breast imaging. Herein, the X-ray source can be arranged parallel to the compression device or the X-ray detector in a linearly displaceable manner. Alternatively or additionally, the X-ray tube can be arranged displaceably on a circular arc, wherein the circular arc is defined about a rotary axis aligned perpendicular to the system axis of a mammography system. This enables three-dimensional X-ray imaging, in particular tomosynthesis, to be performed by means of the mammography system. Generally, tomosynthesis enables the generation of a three-dimensional image from two-dimensional images which were acquired from different angles of the X-ray source relative to the X-ray detector. The two-dimensional and/or three-dimensional images can be part of a tomosynthesis (image) dataset.

The use of tomosynthesis methods for orthopedic applications is an increasingly discussed subject. For example, a tomosynthesis method for orthopedic issues is known from the publication C. Luckner et al, "Parallel-Shift Tomosynthesis for Orthopedic Applications", SPIE Medical Imaging, Houston, 2018.

SUMMARY

The inventor has recognized the problem that the calculation of in particular thicker slices requires the depth information to be adapted to the recording geometry.

Embodiments of the invention disclose a method, an image generating unit, a medical X-ray system, a computer program product and a computer-readable medium, which enable improved determination of slice images.

Embodiments of the invention are directed to a method, an image generating unit, a medical X-ray system, a computer program product and a computer-readable medium.

At least one embodiment of the invention generally relates to a method for determining a slice image of a tomosynthesis recording of an examination object having the steps of recording, of reconstructing and determining. In the recording step, a multiplicity of projection recordings are recorded along a linear trajectory, wherein an X-ray source and an X-ray detector move in parallel opposite to one another along the linear trajectory and the examination object is arranged between the X-ray source and the X-ray detector. In the reconstructing step, a tomosynthesis dataset is reconstructed, wherein the depth information of the examination object is in each case determined along an X-ray beam bundle spanned by the motion along the linear trajectory and the X-ray beam fan of the X-ray source perpendicular to the linear trajectory so that different depth levels in the object parallel to the detection surface are scanned differently. The different scanning is in particular embodied perpendicular to the direction of motion or the linear trajectory. The X-ray beam bundle can be roof-shaped, wherein this is spanned by the X-ray fan perpendicular to the direction of motion and by the linear motion along the linear trajectory. In the determining step, a first slice image with a first slice thickness is determined in a depth level that is substantially parallel to the detection surface of the X-ray detector based on the tomosynthesis dataset.

At least one embodiment of the invention relates to the reconstruction of a tomosynthesis volume and the subsequent depiction of the tomosynthesis volume. The X-ray source and the X-ray detector are moved in parallel along the same direction, wherein the examination object is arranged between the X-ray source and the X-ray detector. The examination object is substantially static, i.e. the examination object is not moved relative to the X-ray source or X-ray detector. During the motion of the X-ray source and the X-ray detector along the examination object, projection datasets are recorded or acquired. The projection datasets are different in each case. The projection datasets comprise different regions of the examination object, wherein temporally and spatially adjacent projection datasets comprise a common overlapping region of the examination object so that adjacent projection datasets comprise information on the examination object from different recording angles of view. This enables depth information on the examination object to be obtained. A reconstruction enables the generation of a tomosynthesis volume dataset based on the projection datasets, wherein the depth information is determined.

At least one embodiment of the invention further relates to an image generating unit for determining a slice image of a tomosynthesis recording of an examination object. The image generating unit comprises a recording unit, a reconstructing unit and a determining unit. The recording unit is embodied to record a multiplicity of projection recordings along a linear trajectory, wherein an X-ray source and an X-ray detector move in parallel opposite to one another along the linear trajectory and the examination object is arranged between the X-ray source and the X-ray detector. The reconstructing unit is embodied to reconstruct a tomosynthesis dataset, wherein the depth information of the examination object is in each case determined along an X-ray beam bundle spanned by the motion along the linear trajectory and the X-ray beam fan of the X-ray source perpendicular to the linear trajectory so that different depth levels in the object parallel to the detection surface are scanned differently. The determining unit is embodied to determine a slice image with a first slice thickness in a depth level that is substantially parallel to the detection surface of the X-ray detector based on the tomosynthesis dataset. The reconstructing unit and the determining unit can be comprised by a computing unit of the medical X-ray system. The advantages of the method according to the invention can be transferred to the device. The image generating unit can further comprise a further determining unit for determining a second slice image, a registration unit for registering, a superimposition unit for superimposing and a depicting unit for depicting. The further units can at least partially be comprised by the computing unit. The depicting unit can in particular be embodied as a display unit, for example in the form of a screen.

At least one embodiment of the invention further relates to a medical X-ray system having an image generating unit according to at least one embodiment of the method for carrying out a method according to the invention. The medical X-ray system is preferably a radiography system. The advantages of the method according to embodiments of the invention can be transferred to the medical X-ray system.

At least one embodiment of the invention further relates to a computer program product with a computer program, which can be loaded directly into a storage facility of a control facility of an X-ray system, with program sections for executing all the steps of the method according to at least one embodiment of the invention when the computer program is executed in the control facility of the X-ray system.

At least one embodiment of the invention further relates to a computer-readable medium on which program sections that can be read and executed by a computing unit are stored for executing all the steps of the method according to at least one embodiment of the invention when the program sections are executed by the computing unit. The computing unit can preferably be comprised by the image generating unit or a processor unit.

At least one embodiment of the invention further relates to a method for determining a slice image of a tomosynthesis recording of an examination object, the method comprising:

recording a plurality of projection recordings along a linear trajectory, wherein an X-ray source and an X-ray detector move in parallel opposite to one another along the linear trajectory and the examination object is arranged between the X-ray source and the X-ray detector;

reconstructing a tomosynthesis dataset, wherein respective depth information of the examination object is respective determined along an X-ray beam bundle spanned by the motion along the linear trajectory and an X-ray beam fan of the X-ray source perpendicular to the linear trajectory so that different respective depth levels in the object parallel to a detection surface of the X-ray detector are respectively scanned differently; and determining a first slice image with a first slice thickness in a depth level, among the respective depth levels, that is substantially parallel to the detection surface of the X-ray detector based on the tomosynthesis dataset.

At least one embodiment of the invention further relates to a image generating unit for determining a slice image of a tomosynthesis recording of an examination object, comprising:

a recording unit to record a multiplicity of projection recordings along a linear trajectory, wherein an X-ray source and an X-ray detector move in parallel opposite to one another along the linear trajectory and the examination object is arranged between the X-ray source and the X-ray detector;

a reconstructing unit to reconstruct a tomosynthesis dataset, wherein respective depth information of the examination object is respectively determined along an X-ray beam bundle spanned by a motion along the linear trajectory and the X-ray beam fan of the X-ray source perpendicular to the linear trajectory so that different respective depth levels in the object parallel to a detection surface of the X-ray detector are respectively scanned differently and a determining unit to determine a slice image with a first slice thickness in a depth level substantially parallel to the detection surface of the X-ray detector based on the tomosynthesis dataset.

At least one embodiment of the invention further relates to a medical X-ray system comprising the image generating unit of an embodiment.

At least one embodiment of the invention further relates to a non-transitory computer program product storing a computer program, directly loadable into a storage facility of a control facility of an X-ray system, including program sections for executing the method of an embodiment when the computer program is executed in the control facility of the X-ray system.

At least one embodiment of the invention further relates to a non-transitory computer-readable medium storing program sections, readable and executable by a computing unit to execute the method of an embodiment when the program sections are executed by the computing unit.

BRIEF DESCRIPTION OF THE DRAWINGS

The following described example embodiments of the invention in more detail with reference to drawings, which show:

FIG. 5 a schematic depiction of the X-ray system according to the invention in a second embodiment.

DETAILED DESCRIPTION OF THE EXAMPLE EMBODIMENTS

Figure 1:
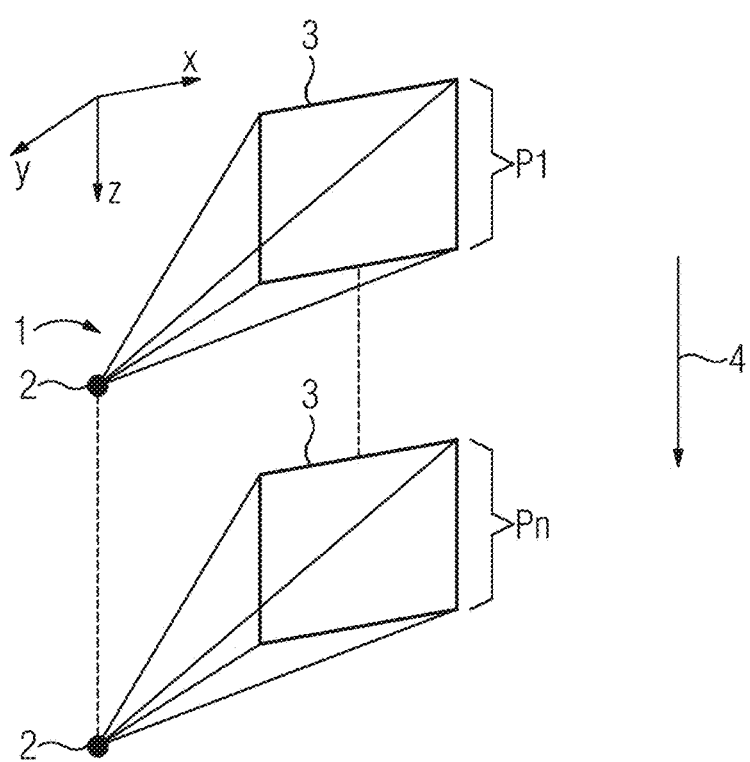
FIG. 1 a schematic depiction of the X-ray system according to the invention in a first embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes;

etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention generally relates to a method for determining a slice image of a tomosynthesis recording of an examination object having the steps of recording, of reconstructing and determining. In the recording step, a multiplicity of projection recordings are recorded along a linear trajectory, wherein an X-ray source and an X-ray detector move in parallel opposite to one another along the linear trajectory and the examination object is arranged between the X-ray source and the X-ray detector. In the reconstructing step, a tomosynthesis dataset is reconstructed, wherein the depth information of the examination object is in each case determined along an X-ray beam bundle spanned by the motion along the linear trajectory and the X-ray beam fan of the X-ray source perpendicular to the linear trajectory so that different depth levels in the object parallel to the detection surface are scanned differently. The different scanning is in particular embodied perpendicular to the direction of motion or the linear trajectory. The X-ray beam bundle can be roof-shaped, wherein this is spanned by the X-ray fan perpendicular to the direction of motion and by the linear motion along the linear trajectory. In the determining step, a first slice image with a first slice thickness is determined in a depth level that is substantially parallel to the detection surface of the X-ray detector based on the tomosynthesis dataset.

The longitudinal body axis of the examination object or a longitudinal axis of the region of interest of the examination object, for example an extremity, can in particular be aligned substantially parallel to the linear trajectory.

The reconstruction of the tomosynthesis dataset can be performed by means of rear projection or a maximum likelihood method. The reconstruction enables the determination of a sectional image or depth information. The tomosynthesis dataset can in particular be an at least partial volume dataset.

The different depth levels in the object parallel to the detection surface are scanned differently. Herein, a depth level, which is arranged closer to the X-ray source is subject to higher spatial scanning than a depth level different therefrom arranged at a greater distance from the X-ray source. Hence, the spatial scanning in the x direction or the x-z level is dependent on the y position of the depth level or a data point of the tomosynthesis dataset.

The first slice image is determined in the x-z direction or the a-z direction. The first slice image and a possible second slice image can in particular be determined by means of forward projection based on the tomosynthesis dataset. The slice thickness can be determined along the y direction. The slice image, in particular the slice center portion, is assigned to a y value.

At least one embodiment of the invention relates to the reconstruction of a tomosynthesis volume and the subsequent depiction of the tomosynthesis volume. The X-ray source and the X-ray detector are moved in parallel along the same direction, wherein the examination object is arranged between the X-ray source and the X-ray detector. The examination object is substantially static, i.e. the examination object is not moved relative to the X-ray source or X-ray detector. During the motion of the X-ray source and the X-ray detector along the examination object, projection datasets are recorded or acquired. The projection datasets are different in each case. The projection datasets comprise different regions of the examination object, wherein temporally and spatially adjacent projection datasets comprise a common overlapping region of the examination object so that adjacent projection datasets comprise information on the examination object from different recording angles of view. This enables depth information on the examination object to be obtained. A reconstruction enables the generation of a tomosynthesis volume dataset based on the projection datasets, wherein the depth information is determined.

The inventor has recognized that the recording geometry means the depth resolution of the tomosynthesis volume is not aligned parallel to a Cartesian coordinate system. Hence, the sampling or scanning of the data can advantageously take place in a specific coordinate system in order to achieve improved slice image data.

In contrast to statically recorded X-ray images and can be described with a "pinhole" camera model, the datasets obtained with the method according to the invention are to be advantageously described with the geometry of a linearly extended X-ray source. Improved image processing and improved depiction and improved registration to datasets sampled or scanned in another way are possible due the knowledge and use of the first or special coordinate system. The registration can also be referred to as image registration. The first slice image dataset and the second slice image dataset can be based on known methods of image registration which are adapted to the geometry with respect to the x-z direction or a-z direction.

According to one embodiment of the invention, the depth information is determined along a path at an angle to a Cartesian spatial direction. The angle is $\alpha=\sin(x/SID)$, wherein the x direction is the Cartesian spatial direction and SID corresponds to the distance between the X-ray source and the X-ray detector in the y direction. Advantageously, improved depth information on the object can be determined compared to a simple projective radiography recording. Advantageously, this angle-dependent depth information can be used in the calculation of slice images in order, in particular in the case of angles that increase in size, to enable a more correct calculation of in particular thick slice images.

According to one embodiment of the invention, the method according to the invention further has the step of further determining. In the further determining step, a second slice image with a second slice thickness that is different from the first slice thickness is determined. The second slice image is determined based on the tomosynthesis dataset. Herein, in particular the depth information along the path at an angle to a Cartesian spatial direction is taken into account. For example, the forward projection can take place along the vector with the angle α, i.e. viewed graphically, the forward projection is performed along the X-ray beam bundle or the fan beam bundle in order to determine the second slice image from the tomosynthesis data. Advantageously, it is possible to reduce or avoid blurring of the object information, in particular in the case of large angles.

According to one embodiment of the invention, the second slice thickness is greater than the first slice thickness. The greater the slice thickness, the more important the effect or the advantages of taking account of the depth information along the path at an angle to the Cartesian spatial direction. Particularly advantageously, thicker slices can be determined, wherein a clear reduction of blurred object information can be enabled.

According to one embodiment of the invention, a plurality of spatially sequential second slice images are determined. Advantageously, items of object information lying close together can be viewed in separate slices so that changes in the object from slice to slice can be observed. In particular, the (depth) position of an item of object information, for example an anatomical property or special feature, can be localized more precisely. Taking account of the depth information along the path at an angle to the Cartesian spatial direction enables the generation of a continuous slice image sequence, which advantageously has a substantially constant image quality.

According to one embodiment of the invention, spatially sequential second slice images comprise overlapping depth information so that the second slice thickness is an integer multiple of the first slice thickness and the distance of the spatially sequential second slice images corresponds to the first slice thickness.

For example, thin slices can be effectively depicted as thicker, in particular in a viewer, by means of pixel averaging, so-called sliding thin slabs. During the determination, it is, for example, possible for a maximum intensity projection (MIP) to be generated, wherein the depth information along a path at an angle to a Cartesian spatial direction is taken into account. In particular, the transitions between the sequential second slice images can be adapted to the recording geometry thus enabling a continuous slice image sequence for connecting regions or overlapping regions.

According to one embodiment of the invention, the second slice image comprises the entire thickness of the examination object. The thickness of the object can preferably be determined in a spatial direction that is different from the linear trajectory. The thickness of the object can in particular be determined along the y direction.

For example, thick slices, in particular a synthetic 2D image which is averaged over the entire object, can be registered and visualized with other datasets in an improved manner. One embodiment is a registration of a long-leg topogram and a computed tomography recording of the knee. Furthermore, improved superimposition of tomosynthesis data with a camera image can be enabled, wherein the camera image can be transferred by rendering onto a 3D surface into the corresponding special coordinate system or the corresponding recording geometry. Advantageously, the depth information identified in the tomosynthesis recording under the influence of the recording geometry according to the invention can be made comparable with image data of a different recording geometry by correspondingly taking into account the different recording geometries or different types of depth information along different paths.

According to one embodiment of the invention, the method according to the invention further has the step of (image) registration. In the registration step, the second slice image is registered with an image dataset from a different imaging modality. Alternatively or additionally, in the registration step, the first slice image can be registered with an image dataset from a different imaging modality. Usual methods can be used for the (image) registration, but herein the change between the Cartesian coordinate system (x,y,z) and the special coordinate system (α,y,z) according to the recording geometry according to the invention should be taken into account. The (image) registration method can in particular be adapted to the change of coordinate system. Advantageously, anatomical regions in the first and/or second slice image can be assigned to the same anatomical region in an image dataset, in particular from a different imaging modality or a different recording geometry.

According to one embodiment of the invention, the method according to the invention further has the step of superimposition. In the superimposition step, the second slice image and the image dataset, in particular from the different imaging modality, are superimposed. Herein, the change between the Cartesian coordinate system (x,y,z) and the special coordinate system (α,y,z) according to the recording geometry according to the invention is taken into account so that the second slice image and the image dataset, in particular from the different imaging modality or a different recording geometry, is taken into account. Advantageously, anatomical details or object information in the same coordinate system can be compared. Particularly advantageously, more reliable and more consistent distance measurements can be enabled based on the second slice image and the image dataset. For example, the second slice image and the image dataset can be superimposed in different colors so that they can both be displayed at the same time. For example, the second slice image and the image dataset can be combined to form one image and hence superimposed. In the case of a long-leg topogram based on the second slice image, for example in the region of the knee, it is possible for a CT dataset to be integrated as an image dataset from a different imaging modality or displayed in this region.

According to one embodiment of the invention, the method according to the invention further has the step of joint depiction. In the joint depiction step, the second slice image and the image dataset, in particular of the other imaging modality, can be jointly depicted on a display unit. Advantageously, it is possible for diagnosis based on the second slice image and the image dataset simultaneously to be enabled. Advantageously, particularly valuable information from the second slice image and the image dataset can in each case be combined to form an overall optimized or improved image display.

At least one embodiment of the invention further relates to an image generating unit for determining a slice image of a tomosynthesis recording of an examination object. The image generating unit comprises a recording unit, a reconstructing unit and a determining unit. The recording unit is embodied to record a multiplicity of projection recordings along a linear trajectory, wherein an X-ray source and an X-ray detector move in parallel opposite to one another along the linear trajectory and the examination object is arranged between the X-ray source and the X-ray detector. The reconstructing unit is embodied to reconstruct a tomosynthesis dataset, wherein the depth information of the examination object is in each case determined along an X-ray beam bundle spanned by the motion along the linear trajectory and the X-ray beam fan of the X-ray source perpendicular to the linear trajectory so that different depth levels in the object parallel to the detection surface are scanned differently. The determining unit is embodied to determine a slice image with a first slice thickness in a depth level that is substantially parallel to the detection surface of the X-ray detector based on the tomosynthesis dataset. The reconstructing unit and the determining unit can be comprised by a computing unit of the medical X-ray system. The advantages of the method according to the invention can be transferred to the device. The image generating unit can further comprise a further determining unit for determining a second slice image, a registration unit for registering, a superimposition unit for superimposing and a depicting unit for depicting. The further units can at least partially be comprised by the computing unit. The depicting unit can in particular be embodied as a display unit, for example in the form of a screen.

At least one embodiment of the invention further relates to a medical X-ray system having an image generating unit according to at least one embodiment of the method for carrying out a method according to the invention. The medical X-ray system is preferably a radiography system. The advantages of the method according to embodiments of the invention can be transferred to the medical X-ray system.

At least one embodiment of the invention further relates to a computer program product with a computer program, which can be loaded directly into a storage facility of a control facility of an X-ray system, with program sections for executing all the steps of the method according to at least one embodiment of the invention when the computer program is executed in the control facility of the X-ray system.

At least one embodiment of the invention further relates to a computer-readable medium on which program sections that can be read and executed by a computing unit are stored for executing all the steps of the method according to at least one embodiment of the invention when the program sections are executed by the computing unit. The computing unit can preferably be comprised by the image generating unit or a processor unit.

FIG. 1 shows an example embodiment of the X-ray system according to the invention 1 in a first embodiment. In particular it describes the scanning or recording geometry of the X-ray system 1. The X-ray system 1 has an X-ray source 2 and an X-ray detector 3, which form an X-ray source-X-ray detector pair. The examination object (not depicted) is arranged between the X-ray source 2 and X-ray detector 3. The X-ray source 2 emits a cone beam or an X-ray beam bundle, which is incident on the examination object and the X-ray detector 3. The X-ray detector 3 has a flat detection surface or level. The detection level is arranged in the x-z level. The surface normal to the detection level of the X-ray detector 3 is arranged parallel to the y-axis. The X-ray source 2 is in particular arranged on the surface normal at a predetermined distance from the X-ray detector 3. During recording, the X-ray detector 3 and the X-ray source 2 move in parallel to one another and simultaneously along the linear trajectory 4 in the same direction, for example the z direction. The X-ray source 2 and the X-ray detector 3 are moved in parallel to the z-axis. The X-ray source 2 and the X-ray detector 3 are shown in a first position P1 and in a n-th position Pn. An X-ray beam bundle is spanned by the motion along the linear trajectory 4 and the X-ray beam fan of the X-ray source 2 perpendicular to the linear trajectory 4.

Figure 2:
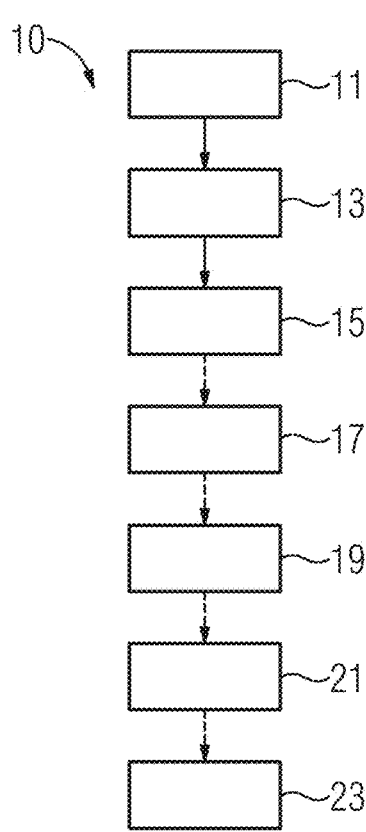
FIG. 2 a schematic depiction of the method according to an embodiment of the invention.

FIG. 2 shows an example embodiment of the method according to the invention 10. The method according to the invention 10 for determining a slice image of a tomosynthesis recording of an examination object has at least the steps of recording 11, of reconstructing 13 and determining 15. In the recording step 11, a multiplicity of projection recordings are recorded along a linear trajectory, wherein an X-ray source and an X-ray detector move in parallel opposite to one another along the linear trajectory and the examination object is arranged between the X-ray source and the X-ray detector. In the reconstructing step 13, a tomosynthesis dataset is reconstructed, wherein the depth information of the examination object is in each case determined along an X-ray beam bundle spanned by the motion along the linear trajectory and the X-ray beam fan of the X-ray source perpendicular to the linear trajectory so that different depth levels in the object parallel to the detection surface are scanned differently. In the determining step 15, a first slice image with a first slice thickness is determined in a depth level that is substantially parallel to the detection surface of the X-ray detector based on the tomosynthesis dataset.

The depth information is determined along a path at an angle to a Cartesian spatial direction. The angle is in particular $\alpha = \sin(x/SID)$, wherein the x direction is the Cartesian spatial direction and SID corresponds to the distance between the X-ray source and the X-ray detector in the y direction.

In one embodiment, the method according to the invention further has the step 17 of further determining. In the further determining step 17, a second slice image with a second slice thickness that is different from the first slice thickness is determined. The second slice thickness is greater than the first slice thickness.

In a special embodiment of the invention, a plurality of spatially sequential second slice images are determined. Spatially sequential second slice images comprise overlapping depth information so that the second slice thickness is an integer multiple of the first slice thickness and the distance of the spatially sequential second slice images corresponds to the first slice thickness. For example, thin slices can be depicted thicker, in particular in a viewer, by means of pixel averaging, so-called sliding thin slabs.

In another special embodiment of the invention, the second slice image covers the entire thickness of the examination object. For example, thick slices, in particular a synthetic 2D image, which is averaged over the entire object can be registered and visualized with other datasets in an improved manner. One example embodiment is an (image) registration of a long-leg topogram and a computed-tomography recording of the knee. Furthermore, improved superimposition of tomosynthesis data with a camera image can be enabled, wherein the camera image can be transferred by rendering onto a 3D surface into the corresponding special coordinate system or the corresponding recording geometry.

In a further embodiment, the method according to the invention further has the step of registration 19. In the registration step 19, the second slice image is registered with an image dataset from a different imaging modality. Alternatively or additionally, in the registration step 19, the first slice image can be registered with an image dataset from a different imaging modality. The method according to the invention can further have the step of superimposition 21. In the superimposition step 21, the second slice image and the image dataset, in particular from the different imaging modality, are superimposed. The method according to the invention can further have the step of joint depiction 23. In the joint depiction step 23, the second slice image and the image dataset, in particular from the different imaging modality, are depicted jointly on a display unit.

Figure 3:
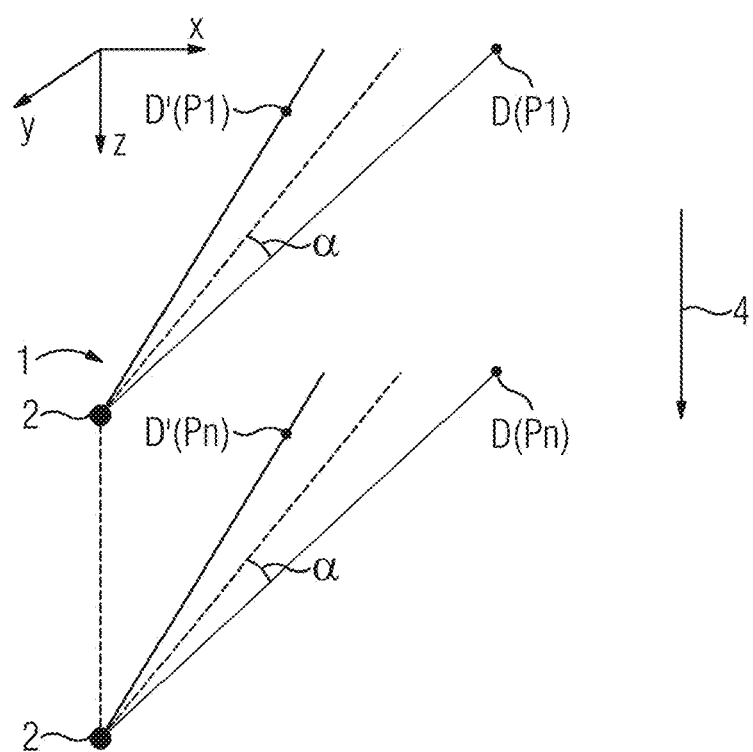
FIG. 3 a schematic depiction of a recording of data points.

FIG. 3 shows an example embodiment of a recording of data points D, D' of depth information. The depth information formed or to be determined is in each case oriented along the angle α in the x-y level. In each case, the angle α for the outermost X-ray beam or path is plotted. For the first position P1, the first value D(P1) for a first item of depth information in the examination object and the first value D'(P1) for a second item of depth information in the examination object are acquired. For the n-th position Pn, the n-th value D(Pn) is acquired for an n-th item of depth information in the examination object and the n-th value D'(Pn) for an n-th item of depth information in the examination object in the same recording geometry, but at a different location in the examination object. At the position P1, the first projection is recorded, here depicted simply as a fan beam. At the position Pn, the n-th projection is recorded. A cone beam or the X-ray beam bundle can also acquire the data points D(P1) and D'(1) in the object from other projections. Depth information or an attenuation value for a voxel can be acquired from a multiplicity of projections, for example by means of rear projection or the maximum likelihood method.

Figure 4:
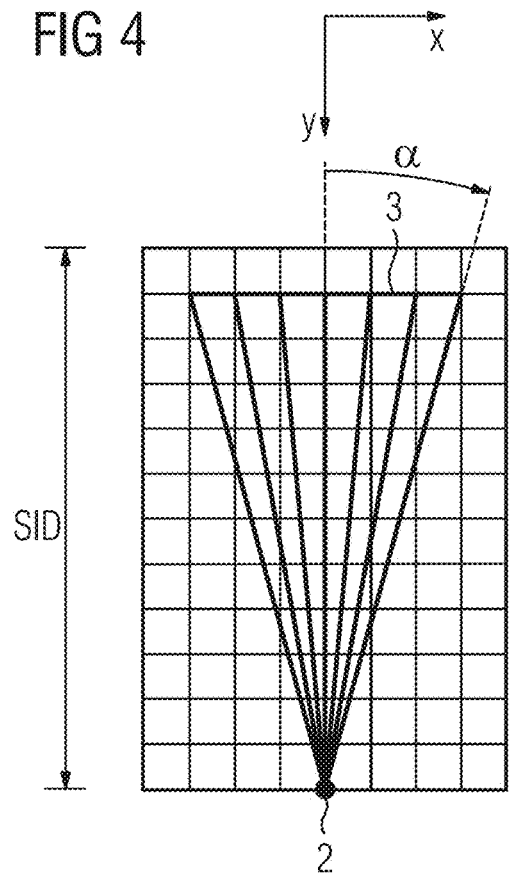
FIG. 4 a schematic depiction of the first coordinate system relative to the Cartesian coordinate system.

FIG. 4 shows an example embodiment of the first coordinate system relative to the Cartesian coordinate system. The first coordinate system is the native coordinate system in the x-y level resulting from the recording geometry. The coordinates of a point between the X-ray source 2 and the X-ray detector 3 is now described by the coordinate transformation (x,y,z) to (α,y,z) with α=sin(x/SID), wherein SID is the distance between the X-ray source 2 and the X-ray detector 3 along the y direction.

FIG. 5 shows an example embodiment of the X-ray system according to the invention 1 in a second embodiment. The X-ray source 2 and the X-ray detector 3 are connected to one another via an image generating unit 30. The image generating unit can be a computing unit and/or or control facility or comprised thereby. The image generating unit 30 comprises the recording unit 31, the reconstructing unit 33 and the determining unit 35. The image generating unit can further comprise the following units: a further determining unit 37, a registration unit 39, a superimposition unit 41 and a depicting unit 43.

Although the invention was illustrated in further detail by the preferred example embodiment, the invention is not restricted by the disclosed examples and other variations can be derived herefrom by the person skilled in the art without departing from the scope of protection of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a slice image of a tomosynthesis recording of an examination object, the method comprising:
    recording a plurality of projection recordings of the examination object along a linear trajectory by moving an X-ray source and an X-ray detector in parallel along the linear trajectory, the X-ray source opposing the X-ray detector, and the examination object being between the X-ray source and the X-ray detector;
    reconstructing a tomosynthesis dataset having depth information of the examination object determined along an X-ray beam bundle which spans along the linear trajectory and along an X-ray beam fan of the X-ray source perpendicular to the linear trajectory such that different depth levels in the examination object parallel to a detection surface of the X-ray detector are scanned differently;
    determining a first slice image based on the tomosynthesis dataset, the first slice image having a first slice thickness in a depth level, from among the different depth levels, the depth level being parallel to the detection surface of the X-ray detector; and
    determining a second slice image having a second slice thickness different from the first slice thickness.

2. The method of claim 1, wherein the depth information is determined along a path having an angle (α) with respect to a Cartesian spatial direction.

3. The method of claim 1, wherein the second slice thickness is greater than the first slice thickness.

4. The method of claim 1, further comprising:
    determining a plurality of spatially sequential second slice images.

5. The method of claim 4, wherein spatially sequential second slice images include overlapping depth information such that the second slice thickness is an integer multiple of the first slice thickness and a distance of the spatially sequential second slice images corresponds to the first slice thickness.

6. The method of claim 3, wherein the second slice thickness is an entire thickness of the examination object.

7. The method of claim 6, further comprising:
    registering the second slice image with an image dataset of a different imaging modality.

8. The method of claim 7, further comprising:
    superimposing the second slice image and the image dataset.

9. The method of claim 8, further comprising:
    jointly depicting the second slice image and the image dataset on a display unit.

10. An image generating unit for determining a slice image of a tomosynthesis recording of an examination object, the image generating unit comprising:
- a recording unit configured to record a plurality of projection recordings of the examination object along a linear trajectory via an X-ray source and an X-ray detector, the X-ray source and the X-ray detector being configured to move in parallel along the linear trajectory, the X-ray source opposing the X-ray detector, and the examination object being between the X-ray source and the X-ray detector;
- a reconstructing unit configured to reconstruct a tomosynthesis dataset having depth information of the examination object determined along an X-ray beam bundle which spans along the linear trajectory and along an X-ray beam fan of the X-ray source perpendicular to the linear trajectory such that different depth levels in the examination object parallel to a detection surface of the X-ray detector are scanned differently;
- a determining unit configured to determine a first slice image based on the tomosynthesis dataset, the first slice image having a first slice thickness in a depth level, from among the different depth levels, the level being parallel to the detection surface of the X-ray detector; and
- a further determining unit configured to determine a second slice image having a second slice thickness different from the first slice thickness.

11. A medical X-ray system comprising the image generating unit of claim 10.

12. A non-transitory computer program product storing a computer program, directly loadable into a storage facility of a control facility of an X-ray system, including program sections for executing the method of claim 1 when the computer program is executed in the control facility of the X-ray system.

13. A non-transitory machine readable medium storing executable instructions that, when executed by one or more processors, causes the one or more processors to perform the method of claim 1.

14. The method of claim 3, further comprising
determining a plurality of spatially sequential second slice images.

15. A non-transitory computer program product storing a computer program, directly loadable into a storage facility of a control facility of an X-ray system, including program sections for executing the method of claim 2 when the computer program is executed in the control facility of the X-ray system.

16. A non-transitory machine readable medium storing executable instructions that, when executed by one or more processors, causes the one or more processors to perform the method of claim 2.

17. An image generating unit for determining a slice image of a tomosynthesis recording of an examination object, the image generating unit comprising:
- one or more processors; and
- a memory storing executable instructions that, when executed by the one or more processors, causes the image generating unit to,
  - record a plurality of projection recordings of the examination object along a linear trajectory via an X-ray source and an X-ray detector, the X-ray source and the X-ray detector being configured to move in parallel along the linear trajectory, the X-ray source opposing the X-ray detector, and the examination object being between the X-ray source and the X-ray detector;
  - reconstruct a tomosynthesis dataset having depth information of the examination object determined along an X-ray beam bundle which spans along the linear trajectory and along an X-ray beam fan of the X-ray source perpendicular to the linear trajectory such that different depth levels in the examination object parallel to a detection surface of the X-ray detector are scanned differently;
  - determine a first slice image based on the tomosynthesis dataset, the first slice image having a first slice thickness in a depth level, from among the different depth levels, the depth level being parallel to the detection surface of the X-ray detector; and
  - determine a second slice image having a second slice thickness different from the first slice thickness.

* * * * *